(12) United States Patent
Blazek

(10) Patent No.: US 7,390,028 B2
(45) Date of Patent: Jun. 24, 2008

(54) MEDICAL TUBING QUICK DISCONNECT APPARATUS

(76) Inventor: Larry M. Blazek, 302 Clarion Ct., Oswego, IL (US) 60543

( * ) Notice: Subject to any disclaimer, the term of this patent is extended or adjusted under 35 U.S.C. 154(b) by 286 days.

(21) Appl. No.: 10/843,891

(22) Filed: May 12, 2004

(65) Prior Publication Data

US 2005/0253390 A1    Nov. 17, 2005

(51) Int. Cl.
*F16L 37/00*    (2006.01)
*A61M 39/10*    (2006.01)

(52) U.S. Cl. .......... 285/317; 285/242; 285/244; 285/308; 285/320; 604/533

(58) Field of Classification Search .......... 285/317, 285/318, 320, 420, 242, 244, 308; 604/533
See application file for complete search history.

(56) References Cited

U.S. PATENT DOCUMENTS

| | | | | |
|---|---|---|---|---|
| 248,262 | A * | 10/1881 | Paulfranz | 137/614.05 |
| 593,190 | A * | 11/1897 | Bernhardt | 285/317 |
| 593,191 | A * | 11/1897 | Bernhardt | 285/280 |
| 621,276 | A * | 3/1899 | Paul | 285/110 |
| 763,317 | A * | 6/1904 | Nelson | 285/320 |
| 1,130,475 | A * | 3/1915 | Campbell | 285/34 |
| 1,150,420 | A * | 8/1915 | Davis et al. | 285/308 |
| 1,480,555 | A * | 1/1924 | Ingram | 285/35 |
| 3,442,541 | A * | 5/1969 | Metz | 403/316 |
| 4,123,091 | A * | 10/1978 | Cosentino et al. | 285/39 |
| 4,326,518 | A * | 4/1982 | Williams | 604/410 |
| 4,405,312 | A | 9/1983 | Gross et al. | |
| 4,889,527 | A | 12/1989 | Herrli | |
| 4,969,879 | A | 11/1990 | Lichte | |
| 5,137,524 | A | 8/1992 | Lynn et al. | |
| 5,265,297 | A * | 11/1993 | Gould et al. | 15/1.7 |
| 5,338,313 | A | 8/1994 | Mollenauer et al. | |
| 5,344,414 | A * | 9/1994 | Lopez et al. | 604/533 |
| 5,447,343 | A * | 9/1995 | Gajewski et al. | 285/317 |
| 5,533,983 | A | 7/1996 | Haining | |
| 5,827,238 | A | 10/1998 | Kelley | |
| 5,848,997 | A | 12/1998 | Erskine et al. | |
| 5,899,888 | A | 5/1999 | Jepson et al. | |
| 5,931,671 | A * | 8/1999 | Hoffman | 433/91 |
| 5,954,708 | A | 9/1999 | Lopez et al. | |
| 5,957,898 | A | 9/1999 | Jepson et al. | |
| 5,971,950 | A | 10/1999 | Lopez et al. | |
| 6,096,011 | A | 8/2000 | Trombley, III et al. | |
| 6,096,024 | A | 8/2000 | Graves et al. | |
| 6,146,374 | A | 11/2000 | Erskine et al. | |
| 6,156,025 | A | 12/2000 | Niedospial, Jr. et al. | |
| 6,183,465 | B1 | 2/2001 | Meier et al. | |
| 6,213,996 | B1 | 4/2001 | Jepson et al. | |
| 6,217,568 | B1 * | 4/2001 | Jepson et al. | 604/533 |
| 6,261,282 | B1 | 7/2001 | Jepson et al. | |

(Continued)

FOREIGN PATENT DOCUMENTS

WO    WO 90/05559    5/1990

(Continued)

*Primary Examiner*—James M Hewitt
(74) *Attorney, Agent, or Firm*—Greenberg Taurig LLP

(57) ABSTRACT

A medical tubing quick disconnect apparatus for connecting two tube ends, is provided with clamping jaws for shutting off flow through one of the tube ends, to enable separation of the components of the disconnect apparatus.

14 Claims, 8 Drawing Sheets

U.S. PATENT DOCUMENTS

| | | |
|---|---|---|
| 6,344,033 B1 | 2/2002 | Jepson et al. |
| 6,423,053 B1 | 7/2002 | Lee |
| 6,572,590 B1 | 6/2003 | Stevens et al. |
| 2002/0115984 A1 | 8/2002 | Guala |
| 2003/0032940 A1 | 2/2003 | Doyle |
| 2003/0060804 A1 | 3/2003 | Vaillancourt |
| 2003/0120260 A1 | 6/2003 | Chu et al. |
| 2003/0181849 A1 | 9/2003 | Castellanos |
| 2003/0187424 A1 | 10/2003 | Chu et al. |

FOREIGN PATENT DOCUMENTS

| | | |
|---|---|---|
| WO | WO 91/16938 | 11/1991 |

* cited by examiner

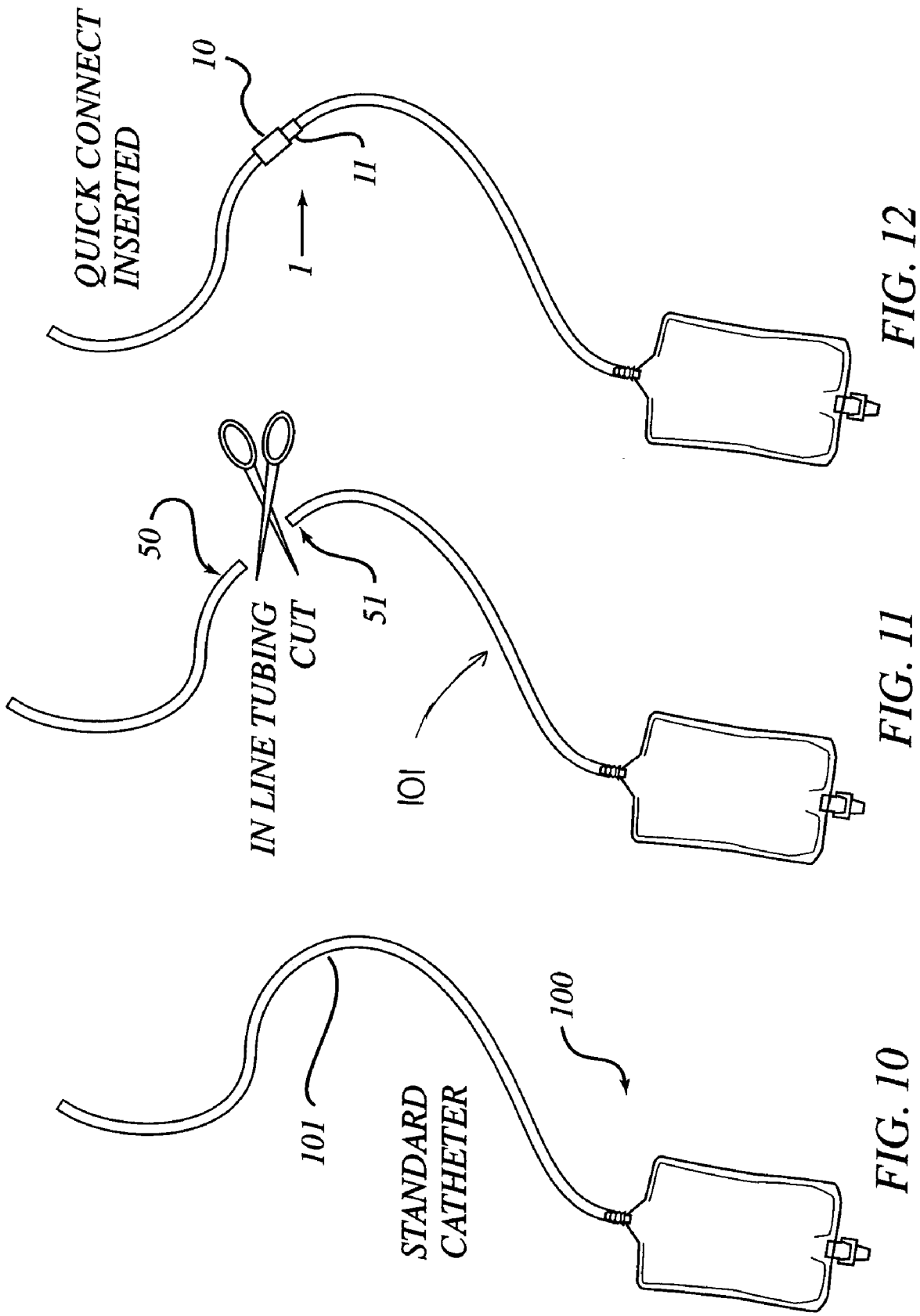

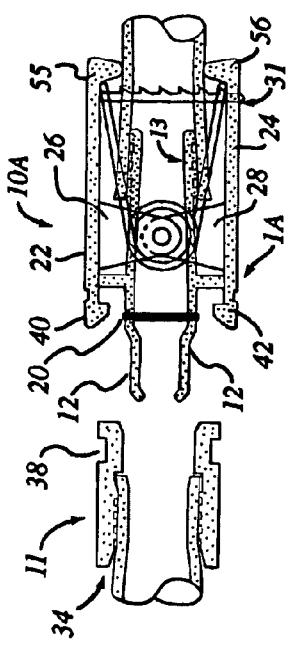
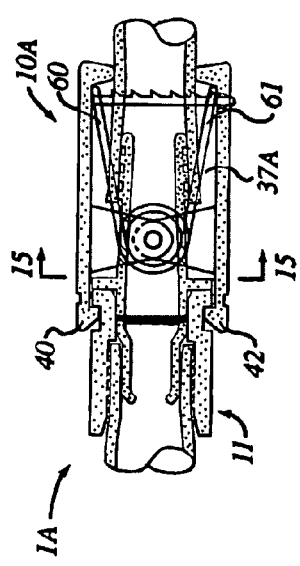
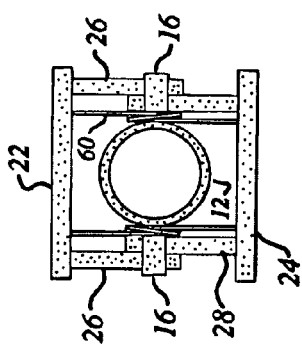
FIG. 13
FIG. 14
FIG. 15

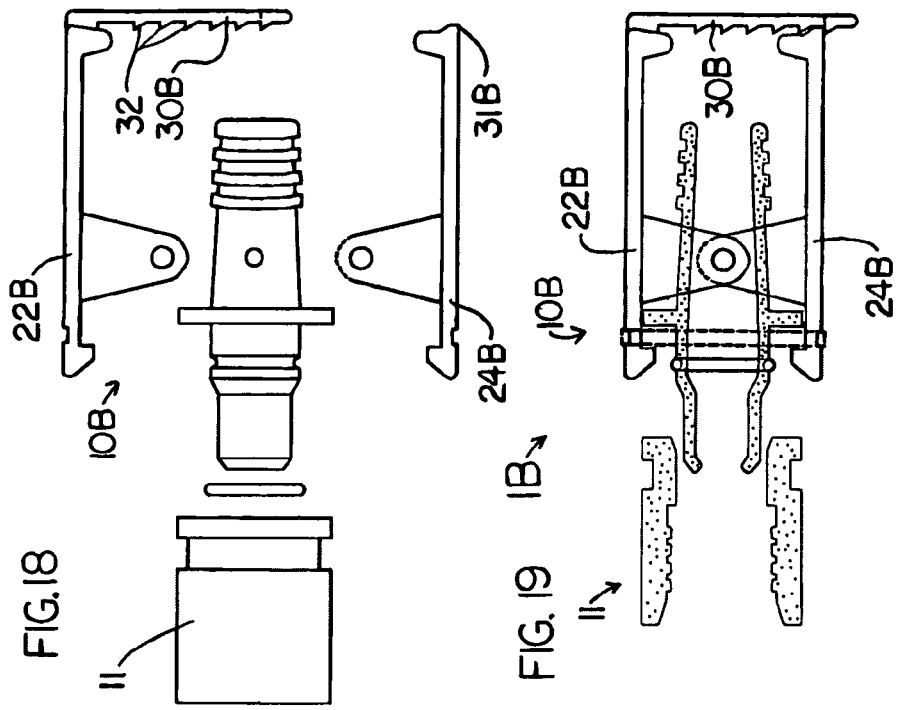
FIG. 18
FIG. 19
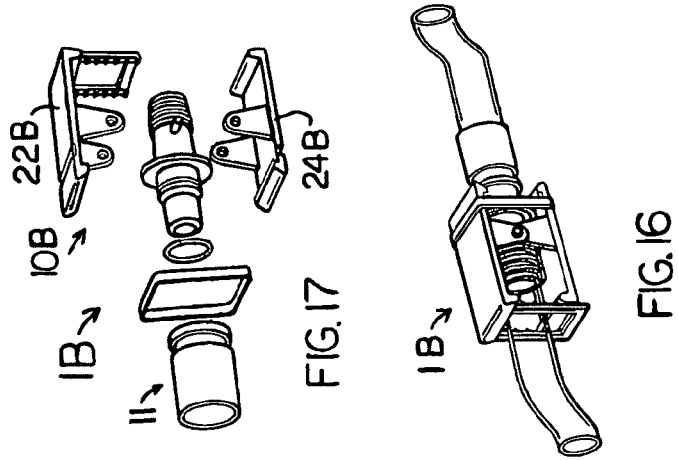
FIG. 17
FIG. 16

MEDICAL TUBING QUICK DISCONNECT APPARATUS

BACKGROUND OF THE INVENTION

1. The Technical Field

The present invention is directed to tubing connection and disconnection apparatus, particular in the environment of medical tubing devices.

2. The Prior Art

When individuals are hospitalized, or otherwise being treated, it is often necessary that such persons be catheterized, in their urinary tract, both during the hospital stay, and often for extended periods thereafter. Typically, the catheterizations involve the actual catheter, a length of uninterrupted tubing, which terminates in a fitting to a collection bag.

Difficulties arise, when the collection bag is full and must be changed, or when switching from a large bag (in-home use) to a smaller bag (for use when moving about or leaving the home). The recuperating patient must either externally clamp or knot the tubing, prior to disconnecting the tubing from the bag and changing the bag.

It would be desirable to provide a device for enabling the rapid disconnection and re-connection of tubing, such as catheter tubing, for example to facilitate the changing from one bag to another, whether for replacing a full bag, or for switching between larger and smaller bags.

It would also be desirable to provide such a tubing disconnect apparatus that has a simple and reliable structure and mode of operation, with positive locking when connected.

It would be further desirable to provide a tubing quick disconnect apparatus that shuts off the flow through the tubing, prior to making the disconnect.

These and other desirable characteristics of the present invention will become apparent in view of the present specification, including claims, and drawings.

SUMMARY OF THE INVENTION

The present invention comprises, in part, a medical tubing quick disconnect apparatus, having a first connection portion. The first connection portion includes a first tubular member, having a longitudinal axis, and having a fitting end operably configured to be connected to a first free tubing end, and a connection end, positioned distal to said fitting end and operably configured to be connected in a fluid tight relationship to a second connection portion. At least one clamp member is configured for pivoting movement about an axis extending transversely to the longitudinal axis, between a clamping position, to clamp a second connection portion to the first connection portion and a release position, to permit separation of the first connection portion from a second connection portion. A biasing member is operably associated with the at least one clamp member, for prompting the at least one clamp member toward said clamping position. A second connection portion includes a second tubular member having a fitting end operably configured to be connected to a second free tubing end, and a connection end, positioned distal to said fitting end of the second tubular member, and operably configured to be connected in substantially fluid-tight relationship to the connection end of the first tubular member.

The at least one clamp member preferably comprises first and second clamp members, said first and second clamp members being disposed on opposite positions about the first tubular member, between the fitting end and the connection end, each of the first and second clamp members being configured for pivoting movement about an axis extending transversely to the longitudinal axis, between a clamping position and a release position. Each of the first and second clamp members preferably includes a substantially planar portion, for facilitating manual grasping and actuation of the first and second clamp members.

The biasing member preferably comprises, in an embodiment of the invention, a resilient band disposed about portions of the first and second clamp members for prompting the first and second clamp members toward their respective clamping positions. At least one of the first and second clamp members is preferably provided with a notch on an outwardly facing surface thereof, for receiving a portion of the resilient band. The biasing member may alternatively comprise a spring, operably associated with at least the first and second clamp members, for prompting the first and second clamp members toward their respective clamping positions.

The at least one clamp member may further include a clamping surface, disposed at a position beyond the fitting end of the first tubular member, such that upon positioning of the at least one clamp member in its release position, the first free tubing end becomes crimped by the clamping surface, for cutting off fluid flow in the first free tubing end. In an embodiment having first and second clamp members, each of the first and second clamp members further preferably includes a clamping surface, disposed at a position beyond the fitting end of the first tubular member, such that upon positioning of the first and second clamp members in their respective release positions, the first free tubing end becomes crimped by the clamping surfaces, for cutting off fluid flow in the first free tubing end.

The first connection portion may further comprise a locking structure, operably associated with the first and second clamp members, for releasably maintaining the first and second clamp members in at least their respective release positions. The locking structure may comprise a hook member, disposed on one of the first and second clamp members, and extending toward the other of the first and second clamp members; and a hook engaging surface, disposed on the other of the first and second clamp members, for releasably engaging the hook member. The hook member may be provided with a plurality of individual hooking elements, for permitting the first and second clamp members to be releasably maintained in a plurality of positions between said clamping positions and said release positions.

The medical tubing quick disconnect apparatus may further comprise at least one barb disposed on the at least one clamp member; and at least one barb engaging surface, disposed on the second tubular member, whereupon when the second tubular member is placed in fluid-tight relationship with the first tubular member, and the at least one clamp member is in its clamping position, the at least one barb engages the at least one barb engaging surface, to preclude separation of the first tubular member from the second tubular member.

In an alternative embodiment of the invention, the medical tubing quick disconnect apparatus comprises a first connection portion, including a first tubular member having a fitting end operably configured to be connected to a first free tubing end, and a connection end positioned distal to said fitting end, and operably configured to be connected in a fluid-tight relationship to a second connection portion. At least one releasable connection element is supported by the first tubular member, and operably configured for releasably engaging the second connection portion and maintaining the second connection portion in a fluid-tight relationship with the first tubular member. The at least one releasable connection element further includes at least one biasing element for prompting the at least one releasable connection element toward a connection configuration, relative to the second connection portion. The at least one releasable connection element further includes a releasable locking mechanism, for releasably maintaining the at least one releasable connection element in a disconnection configuration, against the prompting of the at least one biasing element, to enable separation of the first and second connection portions. A second connection portion includes a second tubular member having a fitting end operably configured to be connected to a second free tubing end, and a connection end positioned distal to the fitting end and operably configured to be connected in a fluid-tight relationship to the connection end of the first connection portion.

The at least one releasable connection element further may comprise at least one flow closure element operably configured to interrupt flow from the first free tubing end into the first connection portion.

The fitting end of the second tubular member may have at least one engagement structure disposed thereon; and the at least one releasable connection element may comprise at least one clamp member, pivotably mounted on the first tubular member for movement between a connection position, wherein the at least one clamp member engages the at least one engagement structure when the first and second connection portions are in a fluid-tight connection relationship to one another, and a disconnect position wherein the at least one clamp member disengages the at least one engagement structure to enable the first and second connection portions to be moved between the connection relationship and a disconnected relationship. The at least one engagement structure may comprise a notch disposed on an outer surface of the second tubular member; and the at least one clamp member is provided with at least one barb for engaging the notch, when the at least one clamp member is in its connection position. The notch may extend around the circumference of the second tubular member, and the at least one clamp member comprises two clamp members disposed on substantially radially opposite sides of the first tubular member, and mounted for pivoting about an axis extending perpendicular to a longitudinal axis of the first tubular member.

The at least one releasable connection element may comprise at least one clamp member, pivotably mounted on the first tubular member for movement between a connection position, wherein the at least one clamp member engages at least one engagement structure disposed on the second connection portion when the first and second connection portions are in a fluid-tight connection relationship to one another, and a disconnect position wherein the at least one clamp member disengages the at least one engagement structure to enable the first and second connection portions to be moved between the connection relationship and a disconnected relationship. The at least one biasing element may comprise a resilient member operably disposed to prompt the at least one clamp member to pivot toward the connection position. The at least one biasing element comprises one of: a resilient elastomeric band, a spring.

The at least one releasable connection element may comprise at least one clamp member, pivotably mounted on the first tubular member for movement between a connection position, wherein the at least one clamp member engages at least one engagement structure disposed on the second connection portion when the first and second connection portions are in a fluid-tight connection relationship to one another, and a disconnect position wherein the at least one clamp member disengages the at least one engagement structure to enable the first and second connection portions to be moved between the connection relationship and a disconnected relationship. The releasable locking mechanism may comprise at least one hook member, disposed on the at least one clamp member, and operably configured to releasably engage a hook engaging surface, operably associated with the first tubular member, for restraining pivoting movement of the at least one clamp member, relative to the first tubular member.

The at least one clamp member may comprise two clamp members disposed on radially opposite sides of the first tubular member, and mounted for pivoting about an axis extending perpendicular to a longitudinal axis of the first tubular member. The at least one hook member is preferably disposed on one of the two clamp members and the hook engaging surface being disposed on the other of the two clamp members, configured for releasable engagement with the at least one hook member.

The at least one releasable connection element may comprise at least one clamp member, pivotably mounted on the first tubular member for movement between a connection position, wherein the at least one clamp member engages at least one engagement structure disposed on the second connection portion when the first and second connection portions are in a fluid-tight connection relationship to one another, and a disconnect position, wherein the at least one clamp member disengages the at least one engagement structure to enable the first and second connection portions to be moved between the connection relationship and a disconnected relationship. The at least one flow closure element preferably comprises a portion of the at least one clamp member being configured to compress the first free tubing end, as the at least one clamp member is moved to its disconnect position. The at least one clamp member may comprise two clamp members disposed on radially opposite sides of the first tubular member, and mounted for pivoting about an axis extending perpendicular to a longitudinal axis of the first tubular member; wherein the at least one flow closure element comprises cooperating portions of the two clamp members being configured to compress the first free tubing end therebetween, as the two clamp members are moved to their disconnect positions.

In a further alternative embodiment of the invention, the medical tubing quick disconnect apparatus comprises a first connection portion, including a first tubular member having a fitting end operably configured to be connected to a first free tubing end, and a connection end positioned distal to said fitting end, and operably configured to be connected in a fluid-tight relationship to a second connection portion. At least one releasable connection element is supported by the first tubular member, and operably configured for releasably engaging the second connection portion and maintaining the second connection portion in a fluid-tight relationship with the first tubular member. The at least one releasable connection element preferably further includes at least one biasing element for prompting the at least one releasable connection element toward a connection configuration, relative to the second connection portion. The at least one releasable connection element may further include at least one flow closure element operably configured to interrupt flow from the first free tubing end into the first connection portion; and a second connection portion, said second connection portion including a second tubular member having a fitting end operably configured to be connected to a second free tubing end, and a connection end positioned distal to the fitting end and operably configured to be connected in a fluid-tight relationship to the connection end of the first connection portion.

The at least one releasable connection element may further comprise a releasable locking mechanism, for releasably maintaining the at least one releasable connection element in a disconnection configuration, against the prompting of the at least one biasing element, to enable separation of the first and second connection portions.

The fitting end of the second tubular member may have at least one engagement structure disposed thereon; and the at least one releasable connection element may comprise at least one clamp member, pivotably mounted on the first tubular member for movement between a connection position, wherein the at least one clamp member engages the at least one engagement structure when the first and second connection portions are in a fluid-tight connection relationship to one another, and a disconnect position wherein the at least one clamp member disengages the at least one engagement structure to enable the first and second connection portions to be moved between the connection relationship and a disconnected relationship. The at least one engagement structure may comprise a notch disposed on an outer surface of the second tubular member; and the at least one clamp member is provided with at least one barb for engaging the notch, when the at least one clamp member is in its connection position. The notch may extend around the circumference of the second tubular member, and the at least one clamp member may comprise two clamp members disposed on substantially radially opposite sides of the first tubular member, and mounted for pivoting about an axis extending perpendicular to a longitudinal axis of the first tubular member.

The at least one releasable connection element may comprise at least one clamp member, pivotably mounted on the first tubular member for movement between a connection position, wherein the at least one clamp member engages at least one engagement structure disposed on the second connection portion when the first and second connection portions are in a fluid-tight connection relationship to one another, and a disconnect position wherein the at least one clamp member disengages the at least one engagement structure to enable the first and second connection portions to be moved between the connection relationship and a disconnected relationship. The at least one biasing element may comprise a resilient member operably disposed to prompt the at least one clamp member to pivot toward the connection position. The at least one biasing element preferably comprises one of: a resilient elastomeric band, a spring.

The at least one releasable connection element may comprise at least one clamp member, pivotably mounted on the first tubular member for movement between a connection position, wherein the at least one clamp member engages at least one engagement structure disposed on the second connection portion when the first and second connection portions are in a fluid-tight connection relationship to one another, and a disconnect position wherein the at least one clamp member disengages the at least one engagement structure to enable the first and second connection portions to be moved between the connection relationship and a disconnected relationship. The releasable locking mechanism may comprise at least one hook member, disposed on the at least one clamp member, and operably configured to releasably engage a hook engaging surface, operably associated with the first tubular member, for restraining pivoting movement of the at least one clamp member, relative to the first tubular member. The at least one clamp member may comprise two clamp members disposed on radially opposite sides of the first tubular member, and mounted for pivoting about an axis extending perpendicular to a longitudinal axis of the first tubular member, with the at least one hook member being disposed on one of the two clamp members and the hook engaging surface being disposed on the other of the two clamp members, configured for releasable engagement with the at least one hook member. The at least one releasable connection element may comprise at least one clamp member, pivotably mounted on the first tubular member for movement between a connection position, wherein the at least one clamp member engages at least one engagement structure disposed on the second connection portion when the first and second connection portions are in a fluid-tight connection relationship to one another, and a disconnect position, wherein the at least one clamp member disengages the at least one engagement structure to enable the first and second connection portions to be moved between the connection relationship and a disconnected relationship; with the at least one flow closure element comprising a portion of the at least one clamp member being configured to compress the first free tubing end, as the at least one clamp member is moved to its disconnect position. The at least one clamp member preferably comprises two clamp members disposed on radially opposite sides of the first tubular member, and mounted for pivoting about an axis extending perpendicular to a longitudinal axis of the first tubular member. The at least one flow closure element preferably comprises cooperating portions of the two clamp members being configured to compress the first free tubing end therebetween, as the two clamp members are moved to their disconnect positions.

BRIEF DESCRIPTION OF THE DRAWINGS

FIG. 10 illustrates a standard catheter hose and collection bag arrangement.

FIG. 11 shows how the tubing of a standard catheter hose and collection bag arrangement is cut for placement of a medical tubing quick disconnect apparatus, in accordance with the principles of the present invention.

FIG. 12 illustrates how a medical tubing quick disconnect apparatus, in accordance with the principles of the present invention, is placed in line in a catheter hose and collection bag arrangement.

FIG. 13 is a side elevation, partially in section of a medical tubing quick disconnect apparatus, according to an alternative embodiment of the invention, wherein an alternative biasing element is provided, and showing the first and second connection portions in their disconnected positions.

FIG. 14 is a side elevation, partially in section of a medical tubing quick disconnect apparatus, according to an alternative embodiment of the invention, wherein an alternative biasing element is provided, and showing the first and second connection portions in their connected positions.

FIG. 15 is a sectional view, taken along line 15-15 of FIG. 14.

FIG. 16 is a perspective view of an alternative embodiment of the invention, having a modified ratcheting mechanism.

FIG. 17 is a perspective exploded view of the apparatus of FIG. 16.

FIG. 18 is an exploded side elevation of the apparatus of FIG. 16.

FIG. 19 is a side elevation, in section of the apparatus of FIG. 16.

DETAILED DESCRIPTION OF THE INVENTION

Figure 1:
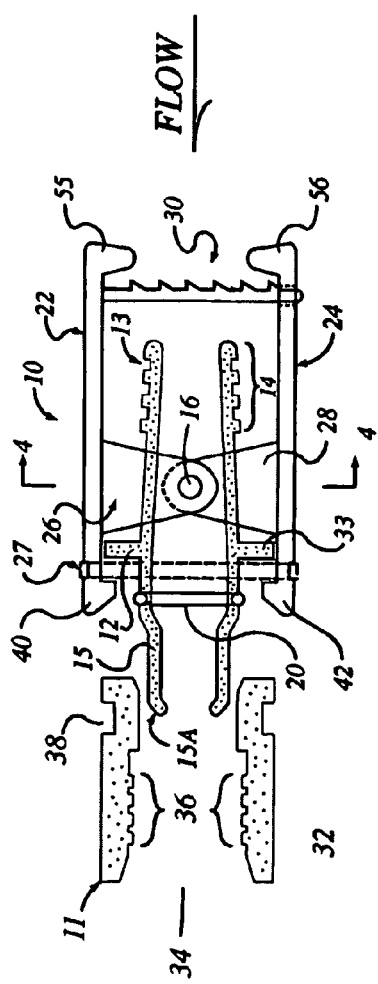
FIG. 1 is a side elevation, in partial section, of elements of the medical tubing quick disconnect apparatus, according to a preferred embodiment of the invention.
Figure 2:
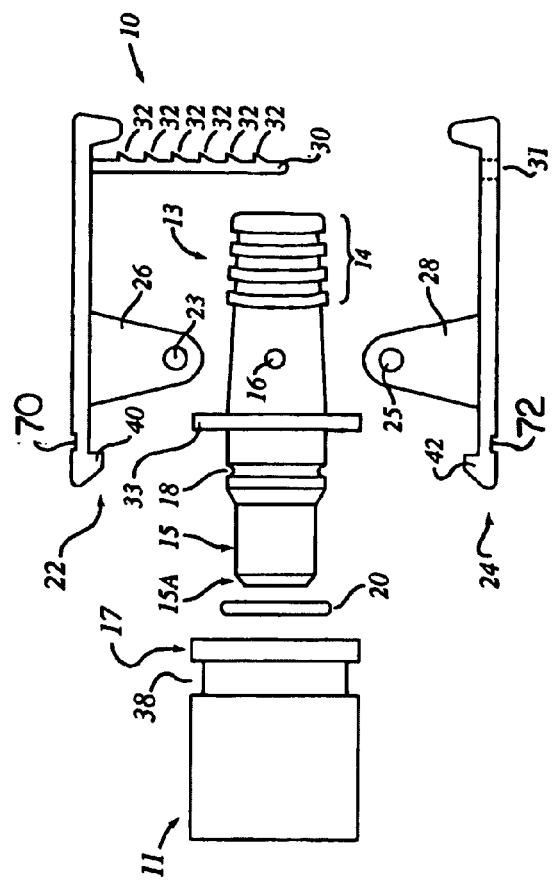
FIG. 2 is an exploded side elevation of elements of the medical tubing quick disconnect apparatus, not connected to tubing, according to the embodiment of FIG. 1.

While this invention is susceptible of embodiment in many different forms, there is shown in the drawings and will be described in detail several specific embodiments, with the understanding that the present disclosure is to be considered an exemplification of the principles of the invention and is not intended to limit the invention to the embodiments illustrated.

Figure 3A:
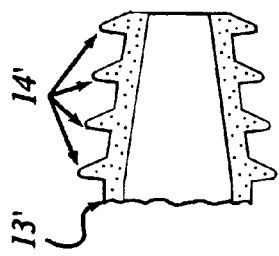
FIG. 3A is an enlarged sectional view of a fitting end for a first connection section of the medical tubing quick disconnect apparatus, according to an alternative embodiment of the invention.
Figure 3:
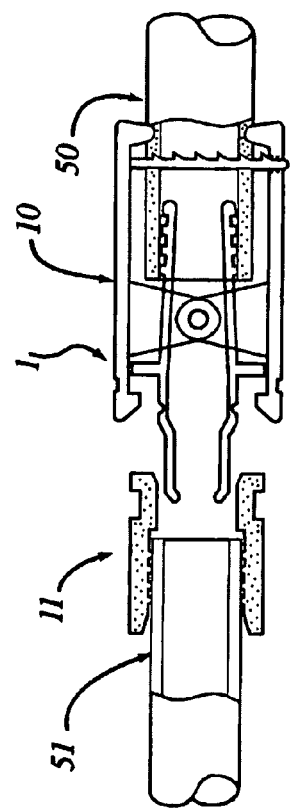
FIG. 3 is a side elevation, in partial section, showing the medical tubing apparatus according to the embodiments of FIGS. 1-2, attached to medical tubing ends.

The medical tubing quick disconnect apparatus 1 (shown assembled in FIG. 3), according to a preferred embodiment of the invention shown in FIGS. 1-3, 4-8, includes first connector portion 10 and second connector portion 11. First connector portion 10 includes rigid hollow tubular element 12, which is provided with fitting end 13, which is configured inserted into an end 50 of a piece of medical tubing, with a forced, friction fit, so as to be not readily dislodged once in place. End 13 may be slightly tapered, and may include circumferential ridges 14, which may help to "grip" the inside surface of the medical tubing. In an alternative embodiment, fitting end 13' may be provided with barbs 14', of triangular cross-section (see, e.g., FIG. 3A). Tubular element 12 also includes connection end 15, which preferably is smaller in diameter than a mid-length portion of tubular element 12, and may further include a tapering tip 15A, the function of which is to facilitate insertion of connection end 15 into second connection portion 11, as described in further detail herein.

Pins 16 (preferably cylindrical) extend outwardly from opposite sides of tubular element 12. Circumferential notch 18 is located between connection end 15 and pins 16, to receive sealing O-ring 20, as shown in FIG. 1. Clamp portions 22, 24 have legs 26, 28, are provided with openings 23, 25, into which pins 16 may be received.

Figure 4:
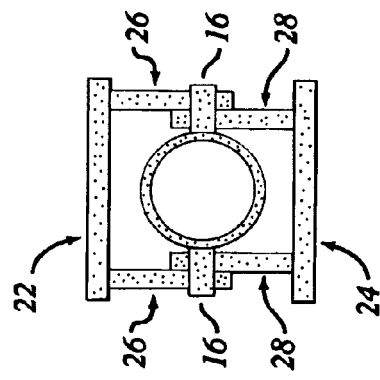
FIG. 4 is a sectional view of the first connection portion of the medical tubing quick disconnect apparatus of the embodiment of FIGS. 1-3, taken along line 4-4 of FIG. 1.
Figure 5:
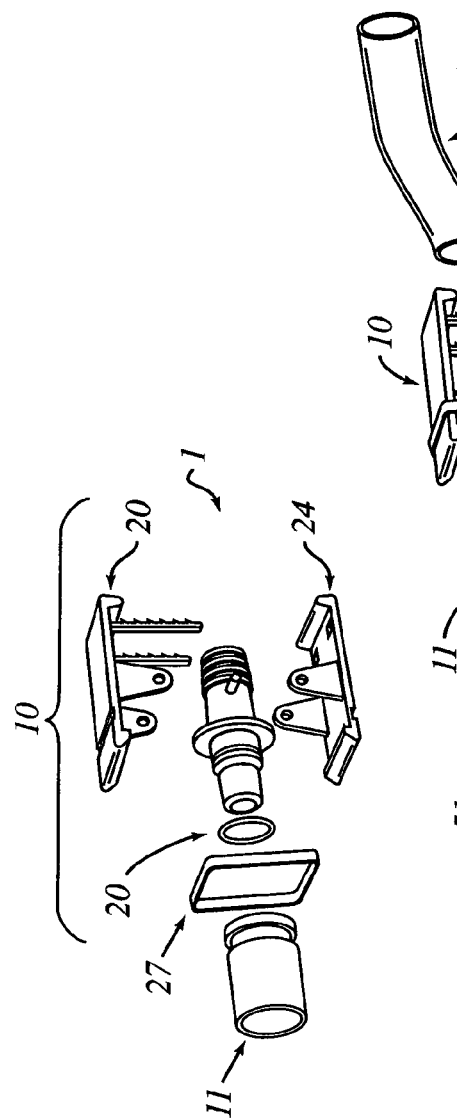
FIG. 5 is an exploded perspective view of the medical tubing quick disconnect apparatus of the embodiment of FIGS. 1-3, 4.
Figure 6:
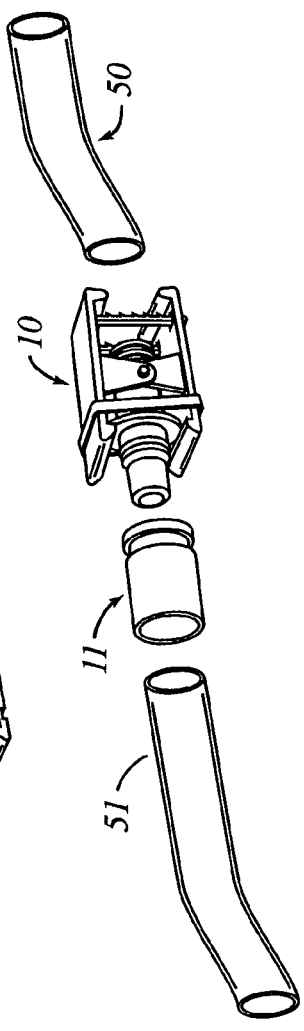
FIG. 6 is a perspective view of the first and second (assembled) connection portions of the medical tubing quick disconnect apparatus of FIGS. 1-3, 4-5, showing their relationship to respective ends of medical tubing to be releasably connected.
Figure 7:
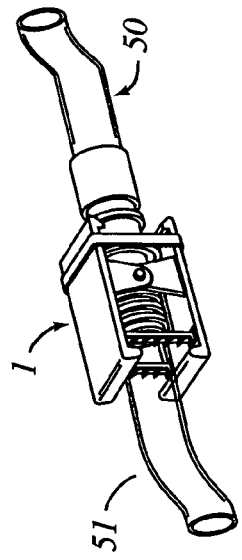
FIG. 7 is a perspective view of a medical tubing quick disconnect apparatus according to the embodiment of FIGS. 1-3, 4-6, reversed relative to the point of view of FIGS. 5 and 6, with the clamp portions shown in their engagement positions.

In the fully assembled medical tubing quick connector apparatus 1, legs 26, 28 are mounted on and pivot about pins 16, so as to render clamp portions 22, 24 to be movable relative to each other in the manner of the jaws of a clothespin. As shown in FIG. 4, in a preferred embodiment of the invention, legs 26 may be to the "outside" of legs 28, although in alternative embodiments, legs 28 may be outside of legs 26, or they may be staggered or alternating. Biasing element 27 (shown in broken lines in FIG. 1), in the embodiment of FIGS. 1-4, is a rubber band, and is preferably positioned around clamp portions 22, 24, between pins 16 and connection end 15 of tubular element 12. Notches 70, 72 may be placed in the outwardly facing surfaces of each of clamp portions 22, 24, for receiving portions of the rubber band, to prevent slippage of the band along the outer surfaces of clamp portions 22, 24. Biasing element 27 biases clamp portions 22, 24, so that the ends of clamp portions 22, 24, bearing barbs 40, 42 tend to be pivoted toward one another, as will be described in further detail herein. Tubular element 12 may be provided with a radially extending flange 33, which may be provided in part, for limiting the amount of pivoting clamp parts 22, 24 may undergo, under the force of biasing element 27.

A ratcheting or locking mechanism is preferably provided, which releasably acts against the force of biasing element 27 to hold clamp portions 22, 24 in various desired positions of pivoting relative to one another. For example, clamp portion 22 may be provided with one or more hook structures 30, extending downwardly toward, and through a corresponding, suitably sized, one or more apertures 31 in clamp portion 24. Each hook structure 30 will be provided with one or more barbs 32. Aperture(s) 31 will have sufficient depth to permit hook structure(s) 30 to be inserted into aperture(s) 31 and permit barbs 32 to pass through, if hook structure 30 is manually or otherwise deflected toward connection end 15 of tubular portion 12.

Hook structure(s) 30 and corresponding barbs 32 will be positioned relative to aperture(s) 31, and oriented such that when a hook structure 30 extends through aperture 31 (to the extent that at least one barb 32 is to the "outside" of clamp portion 24), and unless hook structure 30 is deflected toward pins 16, the at least barb 32 will engage an outside surface of clamp portion 24, adjacent aperture 31, to hold barbs 40, 42 away from one another, and prevent them from being brought toward one another under the action of biasing element 27. If hook structure 30 is deflected toward pins 16, the barb/barbs 32 will clear the edges of aperture(s) 31 distal to pins 16, and permit clamp portions 22, 24 to pivot relative to one another, unless barbed hook structure 30 is deflected to the left (as viewed in FIG. 1) for release of the ratchet.

Second connector portion 11 preferably is in the form of a circumferential tube, having fitting end 34 which preferably has an internal diameter that is slightly less than the outer diameter of the medical tubing to which medical tubing quick disconnect 1 will be connected. Fitting end 34 may be provided with inner ridges 36 for gripping the surface of the end 51 of the medical tubing. Inner ridges 36 may be alternatively in the form of inwardly projecting barbs, analogous to barbs 14' of FIG. 3A. Connection end 17 of second connector portion 11 preferably is provided with outer circumferential notch 38, which is configured to be gripped by the barbs 40, 42 of clamp portions 22, 24. Connection ends 15 and 17 are configured so that when connection end 15 (including sealing O-ring 20) is fully inserted into connection end 17, a relatively air and/or liquid-tight seal is created. The components of medical tubing quick disconnect apparatus 1 are shown in perspective exploded view in FIG. 5. The components of first connection portion 10 are shown assembled in FIG. 6, ready to be attached to end 50 of medical tubing, while second connection portion 11 is ready to be attached to end 51 of medical tubing, which ends 50, 51, have, in a preferred embodiment of the invention, just been severed by cutting, as shown and described hereinafter.

The procedure of attaching the medical tubing quick disconnect apparatus of FIGS. 1-3, 4-12 is relatively straightforward. A medical tubing application, such as a standard catheter/collection bag arrangement 100 attached to tubing 101 (FIG. 10) is first modified by cutting tubing 101 (as shown in FIG. 11), to produce tubing ends 50, 51. Free tubing end 50 is inserted onto fitting end 13 of first connection portion 10, and the other free end 51 is inserted into fitting end 34 of second connection portion 11.

Figure 8:
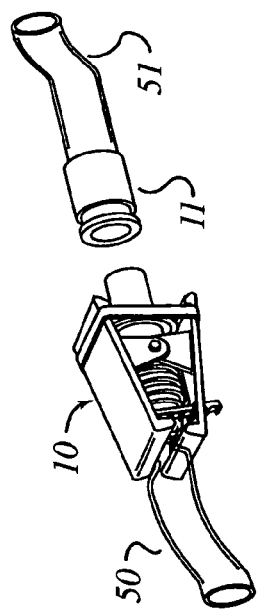
FIG. 8 is a perspective view of a medical tubing quick disconnect apparatus according to the embodiment of FIGS. 1-3, 4-6, reversed relative to the point of view of FIGS. 5 and 6, showing the clamp portions in their disconnect positions.

To connect first connection portion 10 to second connection portion 11, far ends 55, 56 of clamp portions 22, 24 are squeezed toward one another. This causes barbs 40, 42 to separate, permitting fitting end 15 of first connection portion 10 to be inserted into fitting end 34 of second connection portion 11. As the free end(s) of hook structure(s) 30 is/are pushed through aperture(s) 31, barb/barbs 32 "ride" on their angled faces against the distal edges of aperture(s) 31, causing hook structure(s) 30 to be deflected toward pins 16. Continued pressure on far ends 55, 56 (against the force exerted by biasing element 27) will cause barb/barbs 32 to successively pass through aperture(s) 31, permitting clamp portions 22, 24 to rotate relative to one another, as shown in FIG. 8. Release of pressure on far ends 55, 56, permits biasing element 27 to tend to move far ends 55, 56 away from one another, but this movement is prevented by the flat side(s) of barb/barbs 32, bearing against the outside surface(s) of clamp portion 24 adjacent aperture(s) 31.

Figure 9:
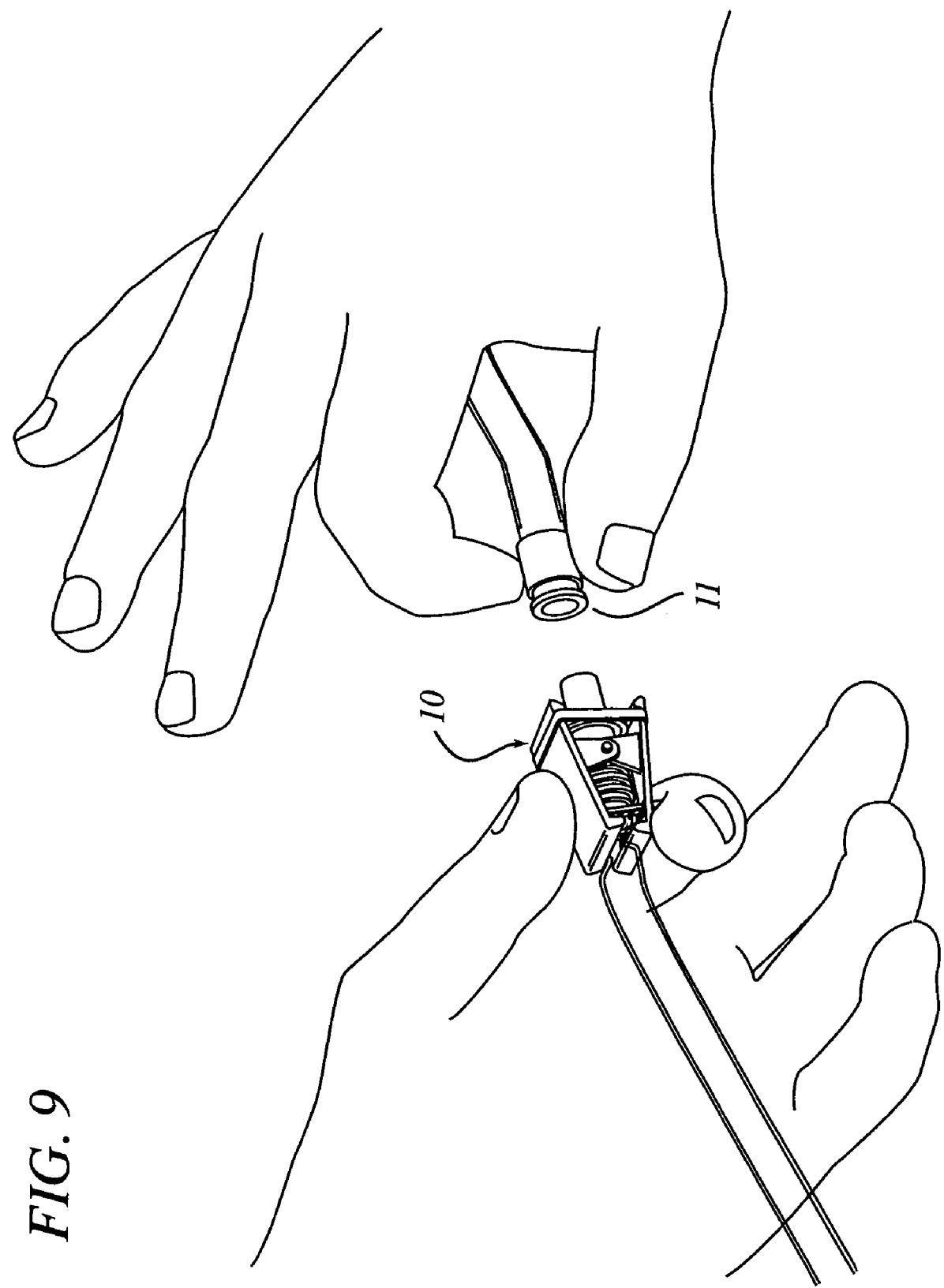
FIG. 9 illustrates how the first and second connection portions of the medical tubing quick disconnect apparatus of FIGS. 1-3, and 4-8 may be manipulated.

FIG. 9 illustrates manipulation of first connection portion 10 and second connection portion 11, which may be either at the point of just connecting or just separating the connection portions.

At this stage in the procedure, fitting end 15 may be inserted into fitting end 34, until sealing O-ring 20 is insertingly received in fitting end 34.

In order to permit clamp portions 22, 24 to pivot relative to one another, such that barbs 40, 42 will be pivoted toward one another and engage circumferential notch 38, manual force is used to deflect hook structure(s) 30 toward pins 16, which, in turn, enables barb/barbs 32 to clear the far edge(s) of aperture(s) 31. As long as hook structure(s) 30 is/are deflected, clamp portions 22, 24, acting under the force of biasing element 27, will pivot to enable barbs 40, 42 to engage second connection portion 11, and establish the connection between tubing ends 50, 51.

In order to separate first connection portion 10 from second connection portion 11, pressure is again applied to far ends 55, 56 of first connection portion 10, until barbs 40, 42 clear notch 38. Upon complete separation, compression of clamp portions 22, 24, causes far ends 55, 56 to compress and preferably seal tubing end 50. As first connection portion 10 is the portion which closes off flow of its corresponding tubing end 50, when the first and second connection portions 10, 11 are separated, it is important that first connection portion 10 be connected to the tubing end which is connected to the source of positive fluid flow.

In addition, preferably the components of clamp portions 22, 24 are sized and proportioned so that far ends 55, 56 close off flow through tubing end 50, prior to the release of notch 38, by barbs 40, 42, so that the physical flow connection between the tube ends 50, 51 is cut off, at the same time as, and preferably before, physical separation of first connection element 10 from second connection element 11, to the point that the fluid-tight connection is broken.

FIGS. 13-15 illustrate medical tubing quick disconnect apparatus 1A, according to an alternative embodiment of the invention. As the embodiment of FIGS. 13-15 are substantially similar to the embodiment of FIGS. 1-3 and 4-12, like elements have been identified by like reference numerals.

FIG. 13 is a side elevation, partially in section of a medical tubing quick disconnect apparatus, according to an alternative embodiment of the invention, wherein an alternative biasing element is provided, and showing the first and second connection portions in their disconnected positions. The components of medical tubing quick disconnect apparatus 1A includes a modified first connection portion 10A and second connection portion 11, which may be identical to second connection portion 11 of the embodiment of FIGS. 1-3, and 4-12. FIG. 14 is a side elevation, in which the first and second connection portions are in their connected configuration. In the embodiment of FIGS. 13-15, the biasing element 37 (a rubber band) of FIGS. 1-3 and 4-12 has been replaced by one or more coiled springs 37A, which may be wound around one or (as shown in FIG. 15) preferably both of pins 16. Preferably, legs 60, 61 of spring 37A are always in compression, regardless of the pivoting orientation of clamp portions, so that spring 37A is at all relative positions of clamp portion 22 to clamp portion 24, tending to force barbs 40, 42 toward one another.

Figure 20:
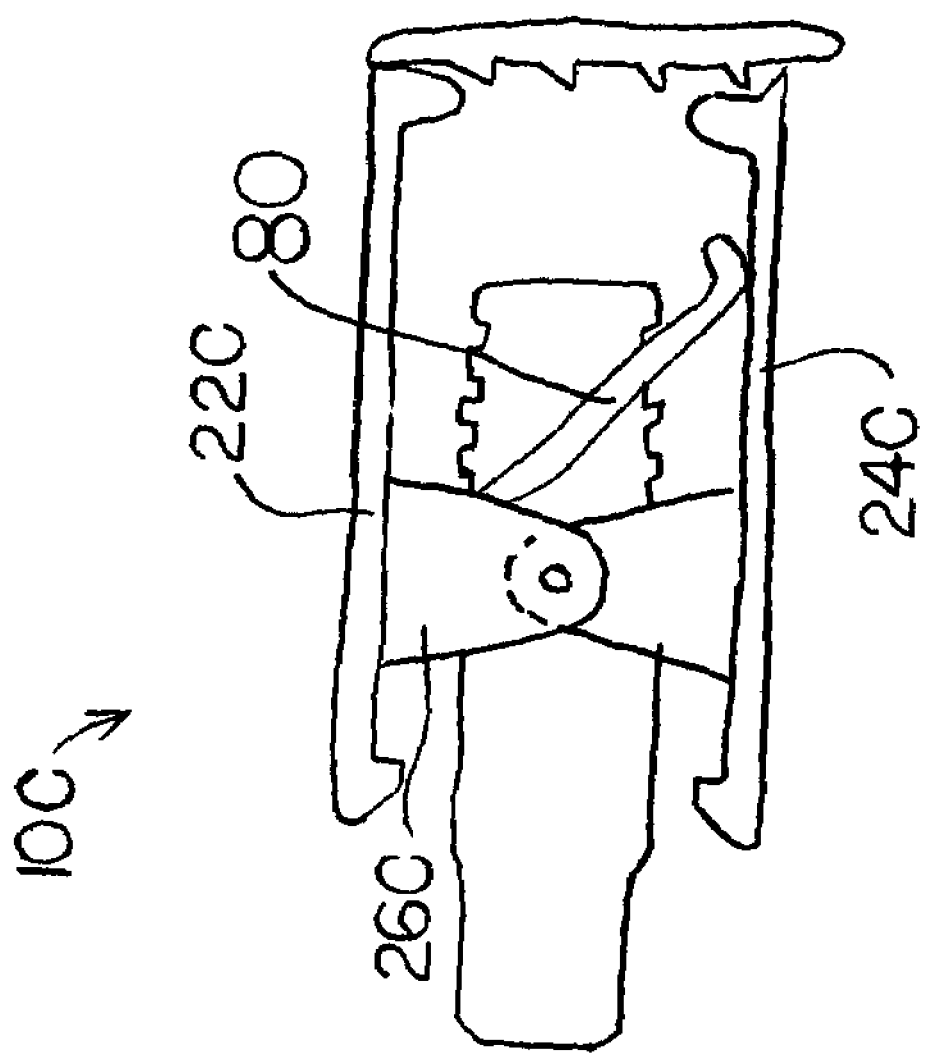
FIG. 20 is a schematic illustration of an alternative embodiment of a first connection portion, having an integrally molded biasing element.

In preferred embodiments of the invention, the components of medical tubing quick disconnect apparatus 1, 1A are fabricated from relatively inexpensive, but easily sterilizable materials, such as medical grade plastic for all the components of FIGS. 1-3 and 4-12 and stainless steel (for the springs of the embodiment of FIGS. 13-15). With regard to the springs, as an alternative construction, the spring could be molded from a sufficiently resilient plastic material, to avoid the need to use metal in the construction. As a still further alternative, in an alternative connection portion 10C (FIG. 20), clamp portion 22C, for example, could be molded with a projecting "tang" 80 (emanating from, e.g., leg(s) 26C) which bears against an inside surface of clamp portion 24C, which serves to provide the biasing force that tends to drive barbs 40, 42 toward one another.

Preferably, the medical tubing quick disconnect apparatus of the present invention will be fabricated from materials such that the disconnect apparatus can be used for as many connect/disconnect cycles, as may be required for the use of the disconnect apparatus for a single patient, and then discarded.

An alternative embodiment of the invention is shown in FIGS. 16-19, wherein elements corresponding to those of the embodiment of FIGS. 1-4 are provided with like reference numerals. In disconnect apparatus 1B of FIGS. 16-19, instead of hook structures 30 which pass through apertures 31 (in FIGS. 1-4), hook structures 30B extend from the end of clamp portion 22B, and teeth 32 engage sharp projecting lips 31B on clamp portion 24B to provide the ratchet structure, which otherwise operates in essentially the same manner as in the embodiment of FIGS. 1-4.

The foregoing description and drawings merely explain and illustrate the invention, and the invention is not limited thereto, except as those skilled in the art who have the present disclosure before them will be able to make modifications and variations therein without departing from the scope of the invention.

What is claimed is:

1. A medical tubing quick disconnect apparatus comprising:
 a first connection portion, said first connection portion including
  a first tubular member, having a longitudinal axis, and having a fitting end operably configured to be connected to a tubing end, and a connection end, positioned distal to said fitting end and operably configured to be connected in a fluid tight relationship to a second connection portion,
    at least one clamp member, said at least one clamp member being configured for pivoting movement about an axis extending perpendicular to and intersecting the longitudinal axis, between a clamping position, to clamp the second connection portion to the first connection portion, and a release position, to permit separation of the first connection portion from said second connection portion, and
    a biasing member, operably associated with the at least one clamp member, for prompting the at least one clamp member toward said clamping position; and
    said second connection portion including
    a second tubular member having a fitting end operably configured to be connected to another tubing end, and a connection end, positioned distal to said fitting end of the second tubular member, and operably configured to be connected in substantially fluid-tight relationship to the connection end of the first tubular member;
    said at least one clamp member further comprising first and second clamp members, said first and second clamp members being disposed on opposite positions about the first tubular member, between the fitting end and the connection end, each of the first and second clamp members being configured for pivoting movement about an axis extending transversely to the longitudinal axis, between a clamping position and a release position;
    the first connection portion further comprising a locking structure, operably associated with the first and second clamp members, for releasably maintaining the first and second clamp members in at least their respective release positions,
    the locking structure further comprising
    a hook member, disposed on one of the first and second clamp members, and extending toward the other of the first and second clamp members; and
    a hook engaging surface, disposed on the other of the first and second clamp members, for releasably engaging the hook member.

2. The medical tubing quick disconnect apparatus according to claim 1, wherein the hook member is provided with a plurality of individual hooking elements, for permitting the first and second clamp members to be releasably maintained in a plurality of positions between said clamping positions and said release positions.

3. The medical tubing quick disconnect apparatus according to claim 1, further comprising:
    at least one barb disposed on the at least one clamp member; and
    at least one barb engaging surface, disposed on the second tubular member, whereupon when the second tubular member is placed in fluid-tight relationship with the first tubular member, and the at least one clamp member is in its clamping position, the at least one barb engages the at least one barb engaging surface, to preclude separation of the first tubular member from the second tubular member.

4. The medical tubing quick disconnect apparatus according to claim 1, wherein each of the first and second clamp members includes a substantially planar portion, for facilitating manual grasping and actuation of the first and second clamp members.

5. The medical tubing quick disconnect apparatus according to claim 1, wherein said biasing member comprises a spring, operably associated with at least the first and second clamp members, for prompting the first and second clamp members toward their respective clamping positions.

6. The medical tubing quick disconnect apparatus according to claim 1, wherein the at least one clamp member further includes a clamping surface, disposed at a position beyond the fitting end of the first tubular member, such that upon positioning of the at least one clamp member in its release position, a first free tubing end becomes crimped by the clamping surface, for cutting off fluid flow in the first free tubing end.

7. The medical tubing quick disconnect apparatus according to claim 1, wherein each of the first and second clamp members further includes a clamping surface, disposed at a position beyond the fitting end of the first tubular member, such that upon positioning of the first and second clamp members in their respective release positions, a first free tubing end becomes crimped by the clamping surfaces, for cutting off fluid flow in the first free tubing end.

8. A medical tubing quick disconnect apparatus comprising:
    a first connection portion, said first connection portion including
    a first tubular member having a fitting end operably configured to be connected to a first free tubing end, and a connection end positioned distal to said fitting end, and operably configured to be connected in a fluid-tight relationship to a second connection portion,
    at least one releasable connection element, supported by the first tubular member, and operably configured for releasably engaging the second connection portion and maintaining the second connection portion in a fluid-tight relationship with the first tubular member,
    the at least one releasable connection element further including at least one biasing element for prompting the at least one releasable connection element toward a connection configuration, relative to the second connection portion,
    the at least one releasable connection element further including a releasable locking mechanism, for releasably maintaining the at least one releasable connection element in a disconnection configuration, against the prompting of the at least one biasing element, to enable separation of the first and second connection portions;
    said second connection portion including
    a second tubular member having a fitting end operably configured to be connected to a second free tubing end, and a connection end positioned distal to the fitting end and operably configured to be connected in a fluid-tight relationship to the connection end of the first connection portion;
    wherein the at least one releasable connection element comprises at least one clamp member, pivotably mounted on the first tubular member for movement between a connection position, wherein the at least one clamp member engages at least one engagement structure disposed on the second connection portion when the first and second connection portions are in a fluid-tight connection relationship to one another, and a disconnect position wherein the at least one clamp member disengages the at least one engagement structure to enable the first and second connection portions to be moved between the connection relationship and a disconnected relationship; and
    the releasable locking mechanism comprises at least one hook member, disposed on the at least one clamp member, and operably configured to releasably engage a hook engaging surface, operably associated with the first tubular member, for restraining pivoting movement of the at least one clamp member, relative to the first tubular member;

wherein the at least one clamp member comprises two clamp members disposed on radially opposite sides of the first tubular member, and mounted for pivoting about an axis extending perpendicular to a longitudinal axis of the first tubular member; and the at least one hook member being disposed on one of the two clamp members and the hook engaging surface being disposed on the other of the two clamp members, configured for releasable engagement with the at least one hook member.

9. The medical tubing quick disconnect apparatus according to claim 8, wherein the at least one releasable connection element further comprises at least one flow closure element operably configured to interrupt flow from the first free tubing end into the first connection portion.

10. A medical tubing quick disconnect apparatus comprising:

a first connection portion, said first connection portion including a first tubular member having a fitting end operably configured to be connected to a first free tubing end, and a connection end positioned distal to said fitting end, and operably configured to be connected in a fluid-tight relationship to a second connection portion, at least one releasable connection element, supported by the first tubular member, and operably configured for releasably engaging the second connection portion and maintaining the second connection portion in a fluid-tight relationship with the first tubular member, the at least one releasable connection element further including at least one biasing element for prompting the at least one releasable connection element toward a connection configuration, relative to the second connection portion, the at least one releasable connection element further including at least one flow closure element operably configured to interrupt flow from the first free tubing end into the first connection portion; and said second connection portion including a second tubular member having a fitting end operably configured to be connected to a second free tubing end, and a connection end positioned distal to the fitting end and operably configured to be connected in a fluid-tight relationship to the connection end of the first connection portion;

the at least one releasable connection element further comprising a releasable locking mechanism, for releasably maintaining the at least one releasable connection element in a disconnection configuration, against the prompting of the at least one biasing element, to enable separation of the first and second connection portions;

wherein the at least one releasable connection element comprises at least one clamp member, pivotably mounted on the first tubular member for movement between a connection position, wherein the at least one clamp member engages at least one engagement structure disposed on the second connection portion when the first and second connection portions are in a fluid-tight connection relationship to one another, and a disconnect position wherein the at least one clamp member disengages the at least one engagement structure to enable the first and second connection portions to be moved between the connection relationship and a disconnected relationship; and the releasable locking mechanism comprises at least one hook member, disposed on the at least one clamp member, and operably configured to releasably engage a hook engaging surface, operably associated with the first tubular member, for restraining pivoting movement of the at least one clamp member, relative to the first tubular member;

wherein the at least one clamp member comprises two clamp members disposed on radially opposite sides of the first tubular member, and mounted for pivoting about an axis extending perpendicular to a longitudinal axis of the first tubular member; and the at least one hook member being disposed on one of the two clamp members and the hook engaging surface being disposed on the other of the two clamp members, configured for releasable engagement with the at least one hook member.

11. A medical tubing quick disconnect apparatus comprising:

a first connection portion, said first connection portion including a first tubular member, having a longitudinal axis, and having a fitting end operably configured to be connected to a first free tubing end, and a connection end, positioned distal to said fitting end and operably configured to be connected in a fluid tight relationship to a second connection portion, at least one clamp member, said at least one clamp member being configured for pivoting movement about an axis extending transversely to the longitudinal axis, between a clamping position, to clamp the second connection portion to the first connection portion, and a release position, to permit separation of the first connection portion from said second connection portion, and a biasing member, operably associated with the at least one clamp member, for prompting the at least one clamp member toward said clamping position; and said second connection portion including a second tubular member having a fitting end operably configured to be connected to a second free tubing end, and a connection end, positioned distal to said fitting end of the second tubular member, and operably configured to be connected in substantially fluid-tight relationship to the connection end of the first tubular member, wherein said at least one clamp member comprises first and second clamp members, said first and second clamp members being disposed on opposite positions about the first tubular member, between the fitting end and the connection end, each of the first and second clamp members being configured for pivoting movement about an axis extending transversely to the longitudinal axis, between a clamping position and a release position, wherein the first connection portion further comprises a locking structure, operably associated with the first and second clamp members, for releasably maintaining the first and second clamp members in at least their respective release positions, and wherein the locking structure comprises a hook member, disposed on one of the first and second clamp members, and extending toward the other of the first and second clamp members; and a hook engaging surface, disposed on the other of the first and second clamp members, for releasably engaging the hook member.

12. The medical tubing quick disconnect apparatus according to claim 11, wherein the hook member is provided with a plurality of individual hooking elements, for permitting the first and second clamp members to be releasably maintained in a plurality of positions between said clamping positions and said release positions.

13. A medical tubing quick disconnect apparatus comprising:
  a first connection portion, said first connection portion including
    a first tubular member having a fitting end operably configured to be connected to a first free tubing end, and a connection end positioned distal to said fitting end, and operably configured to be connected in a fluid-tight relationship to a second connection portion,
    at least one releasable connection element, supported by the first tubular member, and operably configured for releasably engaging the second connection portion and maintaining the second connection portion in a fluid-tight relationship with the first tubular member,
    the at least one releasable connection element further including at least one biasing element for prompting the at least one releasable connection element toward a connection configuration, relative to the second connection portion,
    the at least one releasable connection element further including a releasable locking mechanism, for releasably maintaining the at east one releasable connection element in a disconnection configuration, against the prompting of the at least one biasing element, to enable separation of the first and second connection portions;
  said second connection portion including
    a second tubular member having a fitting end operably configured to be connected to a second free tubing end, and a connection end positioned distal to the fitting end and operably configured to be connected in a fluid-tight relationship to the connection end of the first connection portion,
  wherein the at least one releasable connection element comprises at least one clamp member, pivotably mounted on the first tubular member for movement between a connection position, wherein the at least one clamp member engages at least one engagement structure disposed on the second connection portion when the first and second connection portions are in a fluid-tight connection relationship to one another, and a disconnect position wherein the at least one clamp member disengages the at least one engagement structure to enable the first and second connection portions to be moved between the connection relationship and a disconnected relationship; and
  the releasable locking mechanism comprises at least one hook member, disposed on the at least one clamp member, and operably configured to releasably engage a hook engaging surface, operably associated with the first tubular member, for restraining pivoting movement of the at least one clamp member, relative to the first tubular member,
  wherein the at least one clamp member comprises two clamp members disposed on radially opposite sides of the first tubular member, and mounted for pivoting about an axis extending perpendicular to a longitudinal axis of the first tubular member; and
  the at least one hook member being disposed on one of the two clamp members and the hook engaging surface being disposed on the other of the two clamp members, configured for releasable engagement with the at least one hook member.

14. A medical tubing quick disconnect apparatus comprising:
  a first connection portion, said first connection portion including
    a first tubular member having a fitting end operably configured to be connected to a first free tubing end, and a connection end positioned distal to said fitting end, and operably configured to be connected in a fluid-tight relationship to a second connection portion,
    at least one releasable connection element, supported by the first tubular member, and operably configured for releasably engaging the second connection portion and maintaining the second connection portion in a fluid-tight relationship with the first tubular member,
    the at least one releasable connection element further including at least one biasing element for prompting the at least one releasable connection element toward a connection configuration, relative to the second connection portion,
    the at least one releasable connection element further including at least one flow closure element operably configured to interrupt flow from the first free tubing end into the first connection portion; and
  said second connection portion including
    a second tubular member having a fitting end operably configured to be connected to a second free tubing end, and a connection end positioned distal to the fitting end and operably configured to be connected in a fluid-tight relationship to the connection end of the first connection portion,
  wherein the at least one releasable connection element further comprises a releasable locking mechanism, for releasably maintaining the at least one releasable connection element in a disconnection configuration, against the prompting of the at least one biasing element, to enable separation of the first and second connection portions,
  wherein the at least one releasable connection element comprises at least. one clamp member, pivotably mounted on the first tubular member for movement between a connection position, wherein the at least one clamp member engages at least one engagement structure disposed on the second connection portion when the first and second connection portions are In a fluid-tight connection relationship to one another, and a disconnect position wherein the at least one clamp member disengages the at least one engagement structure to enable the first and second connection portions to be moved between the connection relationship and a disconnected relationship; and
  the releasable locking mechanism comprises at least one hook member, disposed on the at least one clamp member, and operably configured to releasably engage a hook engaging surface, operably associated with the first tubular member, for restraining pivoting movement of the at least one clamp member, relative to the first tubular member, and
  wherein the at least one clamp member comprises two clamp members disposed on radially opposite sides of the first tubular member, and mounted for pivoting about an axis extending perpendicular to a longitudinal axis of the first tubular member; and
  the at least one hook member being disposed on one of the two clamp members and the hook engaging surface being disposed on the other of the two clamp members, configured for releasable engagement with the at least one hook member.

* * * * *